Figure 1:
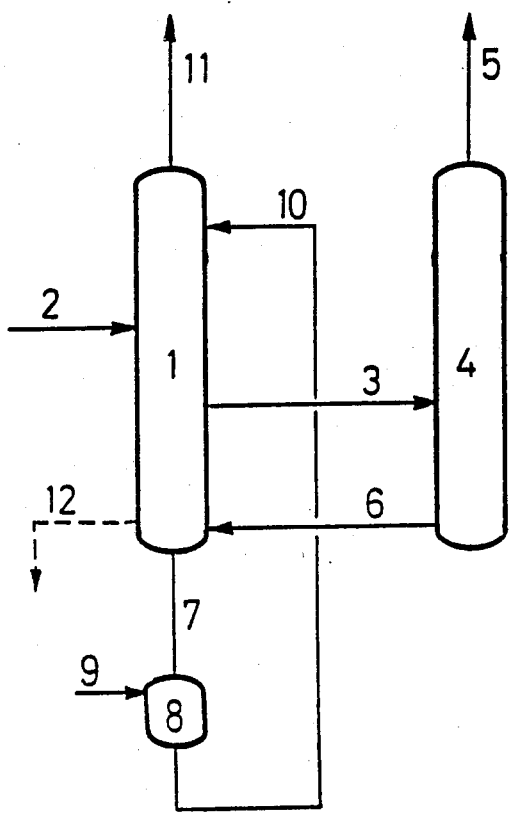

United States Patent [19]

Lindner et al.

[11] Patent Number: 4,647,344

[45] Date of Patent: Mar. 3, 1987

[54] RECOVERY OF ISOPRENE FROM A C5-HYDROCARBON MIXTURE

[75] Inventors: Alfred Lindner, Bobenheim-Roxheim; Ulrich Wagner, Limburgerhof; Klaus Volkamer, Frankenthal; Walter Rebafka, Hirschberg, all of Fed. Rep. of Germany

[73] Assignee: BASF Aktiengesellschaft, Ludwigshafen, Fed. Rep. of Germany

[21] Appl. No.: 662,602

[22] Filed: Oct. 19, 1984

[30] Foreign Application Priority Data

Oct. 21, 1983 [DE] Fed. Rep. of Germany ....... 3338269

[51] Int. Cl.$^4$ ............................................... B01D 3/40
[52] U.S. Cl. ........................................ 203/29; 203/50; 203/74; 203/78; 203/DIG. 19; 203/99; 585/810; 585/865
[58] Field of Search .................. 203/71, 29, 75, 50, 203/74, 78, 27, 99, DIG. 19, DIG. 6; 585/810, 865, 864

[56] References Cited

U.S. PATENT DOCUMENTS

| | | | |
|---|---|---|---|
| 3,038,016 | 6/1962 | Hachmuth | 585/864 |
| 3,510,405 | 5/1970 | Takao et al. | 203/9 |
| 3,557,239 | 1/1971 | Gebhart | 585/810 |
| 3,686,349 | 8/1972 | Schliebs et al. | 585/810 |
| 3,707,575 | 12/1972 | Muller et al. | 203/58 |
| 3,775,259 | 11/1973 | Saino | 203/58 |
| 3,851,010 | 11/1974 | Rescalli et al. | 585/865 |
| 3,860,496 | 1/1975 | Ginnasi et al. | 203/58 |
| 4,401,515 | 8/1983 | Arakawa et al. | 203/84 |
| 4,431,528 | 2/1984 | Schleppinghoff et al. | 585/865 |

FOREIGN PATENT DOCUMENTS

| | | | |
|---|---|---|---|
| 0023370 | 2/1981 | European Pat. Off. | 585/865 |
| 1093413 | 11/1967 | United Kingdom | 585/810 |
| 1137268 | 12/1968 | United Kingdom | 585/810 |
| 1195648 | 6/1970 | United Kingdom | 585/810 |

OTHER PUBLICATIONS

Weissberger, Arnold, "Technique of Organic Chemistry," vol. IV, 2nd Ed. *Distillation*, pp. 424-426 & p. 430.
Bennett, C. O. and Myers, J. E. "Momentum, Heat and Mass Transfer, 2nd Ed., p. 592 & pp. 745-748.

*Primary Examiner*—S. Leon Bashore
*Assistant Examiner*—V. Manoharan
*Attorney, Agent, or Firm*—Keil & Weinkauf

[57] ABSTRACT

Isoprene is recovered from a C5-hydrocarbon mixture containing isoprene, penta-1,3-diene and cyclopentadiene by separating the said mixture by liquid-liquid extraction or extractive distillation with the aid of a selective solvent, in combination with a distillation upstream or downstream from the liquid-liquid extraction or extractive distillation, by a method in which a stream containing penta-1,3-diene and cyclopentadiene is separated off in the upstream or downstream distillation and is catalytically hydrogenated, and the hydrogenated stream is fed to the upper part of the liquid-liquid extraction or extractive distillation.

6 Claims, 2 Drawing Figures

RECOVERY OF ISOPRENE FROM A C₅-HYDROCARBON MIXTURE

The present invention relates to a process for recovering isoprene from a C₅-hydrocarbon mixture containing isoprene, penta-1,3-diene and cyclopentadiene.

It has been disclosed, for example in German Published Application DAS No. 1,807,675, that isoprene can be recovered from a C₅-hydrocarbon mixture containing isoprene and cyclopentadiene by extractive distillation, using a selective solvent. However, in order to obtain very pure isoprene which is suitable for polymerization to polyisoprene, a combination of two extractive distillations and one fractional distillation is required in this process. Furthermore, in order to obtain an isoprene with a sufficiently low cyclopentadiene content, the solvent recovery zone (devolatilizer) of the extractive distillation has to be operated under reduced pressure. This process therefore requires very expensive apparatus and consumes a substantial amount of energy, this energy consumption furthermore being associated with elevated temperatures. Another disadvantage of the conventional process is that the diene mixture which contains penta-1,3-diene, cyclopentadiene and dicyclopentadiene and is produced in substantial amounts during devolatilization in the solvent recovery zone is of little use.

The present invention is intended to improve the procedure and cost-efficiency of the conventional processes.

It is an object of the present invention to provide a process for recovering isoprene from a C₅-hydrocarbon mixture containing isoprene, penta-1,3-diene and cyclopentadiene by liquid-liquid extraction or extractive distillation, wherein the process temperature and the energy consumption can both be kept low.

We have found that these and other objects and advantages are achieved, in accordance with the invention, by a process for recovering isoprene from a C₅-hydrocarbon mixture containing isoprene, penta-1,3-diene and cyclopentadiene by separating the said mixture by liquid- liquid extraction or extractive distillation with the aid of a selective solvent in combination with a distillation upstream or downstream from the liquid-liquid extraction or the extractive distillation, wherein a stream containing penta-1,3-diene and cyclopentadiene is separated off in the upstream or downstream distillation and is catalytically hydrogenated, and the hydrogenated stream is fed to the upper part of the liquid-liquid extraction or the extractive distillation.

In the novel process, the temperature can be kept low in a surprisingly simple manner, since it is possible partly or completely to dispense with devolatilization of solvent laden with penta-1,3-diene and cyclopentadiene and with dicyclopentadiene formed from cyclopentadiene, devolatilization necessitating an elevated process temperature. The hydrogenation products, such as pentane, pentenes, cyclopentane and cyclopentene, which are formed by the hydrogenation of penta-1,3-diene and cyclopentadiene by the novel process can be separated off in a simple manner as useful products, in the distillate from the liquid-liquid extraction or extractive distillation. In the novel process, it is possible to avoid the difficulties that arise in the conventional process as a result of possible dimerization of the cyclopentadiene to dicyclopentadiene and the possible decomposition of dicyclopentadiene with reformation of cyclopentadiene.

The C₅-hydrocarbon mixtures which are to be employed, according to the invention, for the recovery of isoprene and which contain isoprene, penta-1,3-diene and cyclopentadiene are obtained as a hydrocarbon fraction in, for example, the preparation of ethylene and/or propylene by thermal cleavage of a petroleum fraction, eg. liquefied petroleum gas (LPG), naphtha, gas oil or the like, in the presence of steam. Such C₅ fractions are also obtained in the catalytic dehydrogenation of pentanes and/or pentenes. As a rule, the C₅-hydrocarbon mixture contains various types of C₅-hydrocarbons having different degrees of saturation, and may furthermore contain small amounts of various hydrocarbons of less than 5 carbon atoms or of more than 5 carbon atoms, or of both these types. As a rule, the C₅-hydrocarbon mixtures contain, for example, n-pentane, isopentane, pent-1-ene, 2-methylbut-1-ene, 3-methylbut-1-ene, 2-methylbut-2-ene, trans-pent-2-ene, cis-pent-2-ene, isoprene, trans-penta-1,3-diene, cis- penta-1,3-diene, penta-1,4-diene, penta-1-yne, pent-2-yne, isopropenylacetylene, isopropylacetylene, cyclopentane, cyclopentene and cyclopentadiene. The C₅-hydrocarbon mixtures contain, as a rule, from 1 to 25, preferably from 2 to 20, particularly from 5 to 15, % by weight of penta-1,3-diene, but larger or smaller amounts may be present. The cyclopentadiene can be present as such or in dimerized form as dicyclopentadiene, with which it is in thermal equilibrium. The starting C₅-hydrocarbon mixture contains in general from 1 to 35, preferably from 2 to 30, in particular from 5 to 25, % by weight of cyclopentadiene and/or dicyclopentadiene, but larger or smaller amounts may be present.

Examples of selective solvents are carboxamides, such as dimethylformamide, diethylformamide, dimethyl- acetamide and N-formylmorpholine, acetonitrile, furfurol, N-methylpyrrolidone, butyrolactone and acetone and their mixtures with water. Particularly advantageously, N-methylpyrrolidone is used as the selective solvent.

The separation of the C₅-hydrocarbons with the aid of the selective solvent is carried out by means of a liquid-liquid extraction or an extractive distillation; it may be advantageous to use the latter method.

The stream which contains penta-1,3-diene and cyclopentadiene (some or all of which may be present as dicyclopentadiene) and is to be subjected, in accordance with the invention, to the catalyst hydrogenation contains in general from 10 to 95, preferably from 20 to 90, in particular from 30 to 80, % by weight of penta-1,3-diene and from 1 to 90, preferably from 20 to 80, in particular from 50 to 70, % by weight of cyclopentadiene, the percentages being based on the amount of C₅-hydrocarbon in the stream. The hydrogen used for the hydrogenation is in general that which is conventionally employed for a hydrogenation reaction, for example technical-grade hydrogen. The hydrogen can be used in undiluted form, or can be diluted beforehand with an inert gas, eg. nitrogen. Preferably, the hydrogen is used without added inert gas, Where the hydrogen for the hydrogenation is diluted with an inert gas, the volume ratio of an inert gas to hydrogen is in general from 1:10,000 to 4:1, preferably from 1:1,000 to 2.5:1.

The hydrogenation can be carried out in the gas phase or liquid phase, and is preferably carried out in the liquid phase. The stream which contains penta-1,3-diene and cyclopentadiene and is to be hydrogenated can be subjected as such to hydrogenation, but it may be advantageous if this stream contains an inert solvent, preferably the selective solvent used for the liquid-liquid extraction or extractive distillation. It is particularly advantageous to use the selective solvent which is obtained from the devolatilization zone of the liquid-liquid extraction or extractive distillation and which has been partially or completely freed from the hydrocarbons in the said zone; the use of only partially devolatilized selective solvent is preferred. Where dilution with a solvent is effected, the latter is used in general in a concentration of from 60 to 99, preferably from 80 to 98, in particular from 90 to 97, % by weight in the mixture with the hydrocarbon stream being hydrogenated.

The hydrogenation can be carried out adiabatically or isothermally. Advantageously, the reaction is carried out at from 20° to 180° C., preferably from 60° to 150° C., and in general under 1 to 100, preferably from 5 to 50, bar. The stream which contains penta-1,3-diene and cyclopentadiene and is being hydrogenated can be fed cocurrent or countercurrent with respect to the hydrogen used for the hydrogenation. In an advantageous embodiment of the process, the heat of hydrogenation is used for the separation of the $C_5$-hydrocarbon mixture in the liquid-liquid extraction and/or extractive distillation, for example by feeding this heat via a reboiler to the liquid-liquid extraction or extractive distillation.

Advantageously used hydrogenation catalysts are those which contain metals of group VIII of the periodic table and/or their compounds. Examples of suitable metals of group VIII of the periodic table are cobalt, nickel and, preferably, the noble metals, such as palladium and platinum, in particular palladium. It may be advantageous to use the catalysts in the form of supported catalysts. Examples of suitable carriers are active carbon, silica gel, alumina, diatomaceous earth, calcium carbonate and mixtures of these. In general, the content of metal of group VIII of the periodic table is from 0.01 to 5, preferably from 0.1 to 2, % by weight, based on the supported catalyst. The supported catalysts containing a metal of group VIII of the periodic table and/or its compounds can be used without further additives, but it may be advantageous to employ supported catalysts which additonally contain one or more compounds of a further metal.

In the hydrogenation of the stream containing penta-1,3-diene and cyclopentadiene, the former is advantageously hydrogenated to pentenes and/or pentane, and the latter to cyclopentene and/or cyclopentane. The hydrogenated stream is fed to the upper part of the liquid-liquid extraction or extractive distillation, in general at or above the feed of the $C_5$-hydrocarbon mixture to the said extraction or said distillation; a feed in the upper third of the liquid-liquid extraction column or of the extractive distillation column is preferred. In a preferred embodiment, the hydrogenated stream is fed together with the selective solvent to the upper part of the said extraction or said distillation.

Figure 2:
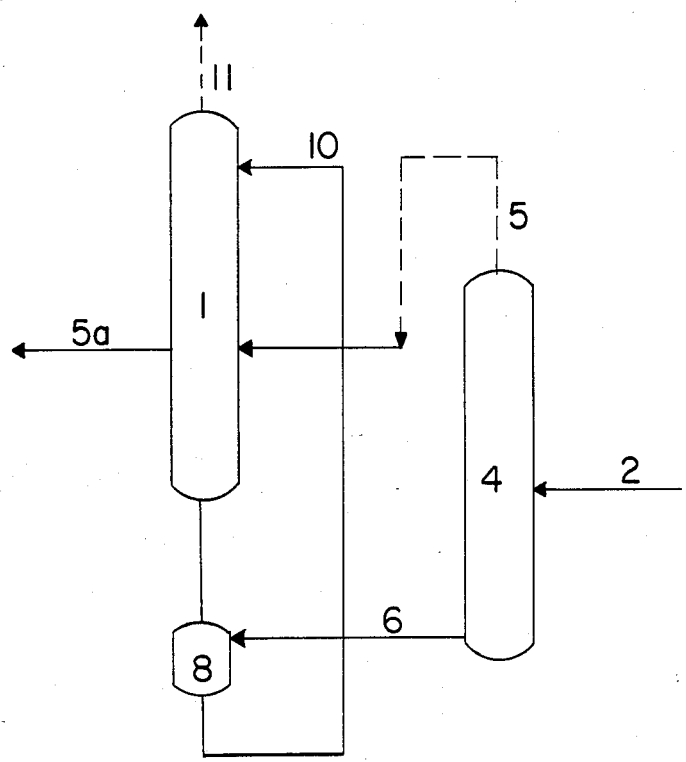

In order that the nature of the invention may be more readily understood, reference is directed to the drawings wherein FIGS. 1 and 2 are flow charts showing the embodiments of the invention.

In an embodiment of the novel process as shown in FIG. 2, for example, the starting $C_5$-hydrocarbon mixture is first distilled in a distillation zone 4 via line 2, an isoprene-containing stream being taken off at the top of the said zone via line 5, and a stream containing penta-1,3-diene and cyclopentadiene being removed at the bottom of this zone via line 6. The latter stream is then catalytically hydrogenated in a hydrogenation zone 8, and the hydrogenated stream is fed to the upper part of a liquid-liquid extraction or extractive distillation column 1 via line 10. The isoprene-containing stream taken off at the top of the upstream distillation zone via line 5 is advantageously fed to the middle section of the said extraction or said distillation column 1, the middle section generally extending from the lower fifth to the upper fifth, preferably from the lower fourth to the upper fourth, in particular from the lower third to the upper third, of the liquid-liquid extraction zone or extractive distillation zone. The $C_5$-hydrocarbons fed to the middle section of the liquid-liquid extraction or extractive distillation are separated into a distillate via line 11 containing those hydrocarbons, eg. n-pentane, isopentane, pent-1-ene, 3-methylbut-1-ene, 2-methylbut-2-ene, pent-2-ene, cyclopentane and cyclopentene, which are less soluble in the selective solvent than is isoprene, a side stream via line 5a consisting of isoprene, and a stream containing those hydrocarbons, eg. 1,3-pentadiene, 1,4-pentadiene, but-2-yne, $C_5$-acetylenes, cyclopentadiene and cyclopentene, which are more soluble in the selective solvent than is isoprene.

In another embodiment of the novel process, for example, the starting $C_5$-hydrocarbon mixture is first separated, by liquid-liquid extraction or extractive distillation, into a distillate containing those hydrocarbons which are less soluble in the selective solvent than is isoprene, a stream containing isoprene, penta-1,3-diene and cyclopentadiene, and a stream containing those hydrocarbons which are more soluble in the selective solvent than is isoprene. In this procedure as shown in FIG. 1, the starting $C_5$-hydrocarbons mixture is generally fed via line 2 to the middle zone of the liquid-liquid extraction or extractive distillation column 1, consisting of a rectifying section, a stripping section and a devolatilization section, in general to a zone which extends from the lower fifth to the upper fifth, preferably from the lower fourth to the upper fourth, in particular from the lower third to the upper third, of the liquid-liquid extraction zone or extractive distillation zone. The stream containing isoprene, penta-1,3-diene and cyclopentadiene is advantageously taken off via line 3 at a point which lies below the feed of the starting $C_5$-hydrocarbon mixture and above the bottom, while the stream conating those hydrocarbons which are more soluble in the selective solvent is advantageously removed at the bottom of the said extraction or said distillation. The stream which contains isoprene, penta-1,3-diene and cyclopentadiene and may also contain selective solvent entrained in proportion to its vapor pressure is separated in a distillation zone 4, a stream consisting of isoprene being taken off at the top of the distillation zone 4 via line 5, and a stream containing penta-1,3-diene and cyclopentadiene being removed at the bottom of the said zone 4 via line 6. This zone is preferably operated as a fractional distillation, but may also be operated as an extractive distillation. The stream which contains penta-1,3-diene and cyclopentadiene and is removed at the bottom of the distillation zone 4 is catalytically hydrogenated in a hydrogenation zone 8 to which hydrogen is fed via line 9, and the hydrogenated stream is fed to the upper part of the liquid-liquid extraction or extractive distillation via line 10, advantageously at a point above the feed of the starting $C_5$-hydrocarbon mixture. It may be advantageous if the said stream removed from the bottom of the distillation zone 4 is combined with the bottom product of the liquid-liquid extraction or extractive distillation column 1, the combined streams are fed to the hydrogenation zone 8 via line 7 for catalytic hydrogenation, and the hydrogenated stream is fed to the upper part of the liquid-liquid extraction or extractive distillation, as described above. However, it is also possible to add the said stream taken off from the bottom of the distillation zone to the selective solvent removed, which has been partially or completely devolatilized, and then to feed the combined stream for catalytic hydrogenation; preferably, the said stream removed from the bottom is added to the partially devolatilized selective solvent.

Isoprene is a useful starting material, for example for the preparation of vitamins, scents and rubber.

The Example which follows illustrates the invention.

EXAMPLE

A starting $C_5$-hydrocarbon mixture having the composition below was fed, via line 2, into an extractive distillation 1 as shown in FIG. 1 consisting of a rectifying section, a stripping section and a devolatilization section and operated with water-containing N-methylpyrrolidone (NMP) (8% by weight of $H_2O$) as the selective solvent:
- isoprene; 18% by weight,
- penta-1,3-diene; 10% by weight,
- cyclopentadiene; 16% by weight,
- pentanes; 30% by weight,
- pentenes and small amounts of $C_4$- and $C_6$-hydrocarbons; 26% by weight.

The bottom temperature in the extractive distillation was from 110 to 130° C. A stream which contained penta-1,3-diene and cyclopentadiene was removed via take-off line 3 of the extractive distillation, and was separated, in the distillation column 4, into an isoprene stream, which was taken off at the top via line 5, and a stream which was taken off at the bottom via line 6 and contained penta-1,3-diene and cyclopentadiene and also contained selective solvent entrained in proportion to its vapor pressure. The bottom product of the distillation was combined with the bottom product of the extractive distillation by feeding into the bottom of the extractive distillation. A stream containing penta-1,3-diene, cyclopentadiene and about 95% by weight of selective solvent was taken off at the bottom of the extractive distillation, via line 7, and was hydrogenated over a palladium-containing alumina supported catalyst in the hydrogenation reactor to which hydrogen was fed via line 9, penta-1,3-diene being hydrogenated to pentenes and pentane, and cyclopentadiene to cyclopentene and cyclopentane. In the hydrogenation reactor, the temperature was maintained at 130° C., and the pressure at 30 bar. The hydrogenated stream removed from the hydrogenation reactor was fed to the top of the extractive distillation via line 10. A distillate containing pentanes, pentenes, cyclopentane and cyclopentene was taken off at the top of the extractive distillation, via line 11. The amount of selective solvent circulating through line 7, the hydrogenation reactor and line 10 was controlled so that the penta-1,3-diene and cyclopentadiene present in the feed 6 to the extractive distillation remained in solution at a bottom temperature of 110–130° C. in the extractive distillation.

In a comparative experiment, the procedure described in the example above was followed, except that the hydrogenation was bypassed by connecting lines 7 and 10. In this procedure, the concentration of penta-1,3-diene and cyclopentadiene increased greatly in the extractive distillation. Hence, in order to remove penta-1,3-diene and cyclopentadiene from the bottom of the extractive distillation 1 (after line 12 had been opened), it was necessary for the bottom temperature in the said distillation to be increased sharply in order to achieve adequate stripping-off of the pentadienes. In fact, under an operating pressure of 1.5 bar, the bottom temperature in 1 had to be increased to above 200° C. when anhydrous NMP was used as the selective solvent, and to about 150° C. when water-containing NMP (8% by weight of $H_2O$) was used. However, high temperatures promote dimerization and polymerization of the dienes. Although the bottom temperature could be reduced by lowering the operating pressure to below atmospheric pressure, this made it necessary, on the one hand, to use a compressor or a refrigerator, while on the other hand the use of these apparatuses increased the possibility of oxygen being introduced. However, oxygen is an effective initiator of extremely troublesome polymerizations in isoprene plants.

We claim:

1. A process for recovering isoprene from a $C_5$-hydrocarbon mixture containing isoprene, penta-1,3-diene and cyclopentadiene which comprises
   (a) distilling the $C_5$-hydrocarbon mixture in a distillation zone,
   (b) taking off an isoprene-containing stream at the top of the distillation zone,
   (c) removing a stream containing penta-1,3-diene and cyclopentadiene at the bottom of the distillation zone,
   (d) catalytically hydrogenating the stream containing penta-1,3-diene and cyclopentadiene in a hydrogenation zone,
   (e) feeding the hydrogenated stream to the upper part of an extractive distillation,
   (f) feeding the isoprene-containing stream taken off at the top of the distillation zone according to step (b) to the middle section of the extractive distillation,
   (g) separating the streams in steps (e) and (f) with the aid of a selective solvent by extractive distillation,
   (h) withdrawing a sidestream consisting of isoprene.

2. A process for recovering isoprene from a $C_5$-hydrocarbon mixture containing isoprene, penta-1,3-diene and cyclopentadiene which comprises
   (a) separating the $C_5$-hydrocarbon mixture, by extractive distillation with the aid of a selective solvent,
   (b) withdrawing a sidestream containing isoprene, penta-1,3-diene and cyclopentadiene from (a) and separating said stream in a distillation zone,
   (c) taking off a stream consisting of isoprene at the top of the distillation zone, and
   (d) removing a stream containing penta-1,3-diene and cyclopentadiene at the bottom of the distillation zone,
   (e) catalytically hydrogenating the steam containing penta-1,3-diene and cyclopentadiene in a hydrogenation zone, and
   (f) feeding the hydrogenated stream to the upper part of the said extractive distillation.

3. The process of claim 1, wherein the stream containing penta-1,3-diene and cyclopentadiene is diluted with the selective solvent and then hydrogenated catalytically, and the hydrogenated stream diluted with the selective solvent is fed to the upper part of the extractive distillation.

4. The process of claim 2, wherein the stream containing penta-1,3-diene and cyclopentadiene is diluted with the selective solvent and then hydrogenated catalytically, and the hydrogenated stream diluted with the selective solvent is fed to the upper part of the extractive distillation.

5. The process of claim 1, wherein the heat of hydrogenation is used in the extractive distillation.

6. The process of claim 2, wherein the heat of hydrogenation is used in the extractive distillation.

* * * * *